United States Patent
Itoh

(10) Patent No.: US 7,195,737 B2
(45) Date of Patent: *Mar. 27, 2007

(54) SPECIMEN CENTRIFUGE SYSTEM

(76) Inventor: Teruaki Itoh, 5-25, Kokaihommachi, Kumamoto-ken, Kumamoto (JP)

( * ) Notice: Subject to any disclaimer, the term of this patent is extended or adjusted under 35 U.S.C. 154(b) by 155 days.

This patent is subject to a terminal disclaimer.

(21) Appl. No.: 10/686,631

(22) Filed: Oct. 17, 2003

(65) Prior Publication Data
US 2004/0089737 A1 May 13, 2004

(30) Foreign Application Priority Data
Oct. 31, 2002 (JP) ............................. 2002-318702

(51) Int. Cl.
G01N 9/30 (2006.01)

(52) U.S. Cl. .................... 422/72; 422/65; 436/45; 436/47; 436/48; 494/16

(58) Field of Classification Search ............. 422/68.1, 422/72, 63, 65, 99, 101, 104; 436/43, 45, 436/47, 48; 494/7, 16, 20, 84
See application file for complete search history.

(56) References Cited

U.S. PATENT DOCUMENTS 5,419,871 A * 5/1995 Muszak et al. ............. 422/63
5,523,056 A * 6/1996 Miller ........................ 422/64
5,623,415 A * 4/1997 O'Bryan et al. ............ 700/225
5,769,775 A * 6/1998 Quinlan et al. ............. 494/10
5,814,276 A * 9/1998 Riggs ......................... 422/65
6,060,022 A * 5/2000 Pang et al. .................. 422/65
6,458,324 B1* 10/2002 Schinzel ..................... 422/65
6,589,789 B1* 7/2003 Hubert et al. ............... 436/45

FOREIGN PATENT DOCUMENTS

JP  01-189562   *  7/1989
JP  2000-84436     3/2000

* cited by examiner

Primary Examiner—Maureen M. Wallenhorst
(74) Attorney, Agent, or Firm—Nixon & Vanderhye P.C.

(57) ABSTRACT

A specimen centrifuge system includes a centrifuge unit including a plurality of specimen centrifuges which are stacked in a plurality of layers in a vertical direction, a rack conveyor which is provided along a horizontal conveyance line, and a rack elevator which is provided along a vertical conveyance line. The rack elevator has a robot arm device which moves the specimen-container rack from the rack conveyor to the rack elevator and from the rack elevator to the rack conveyor and moves the specimen-container rack from the rack elevator to one of the specimen centrifuges and from one of the specimen centrifuges to the rack elevator.

4 Claims, 6 Drawing Sheets

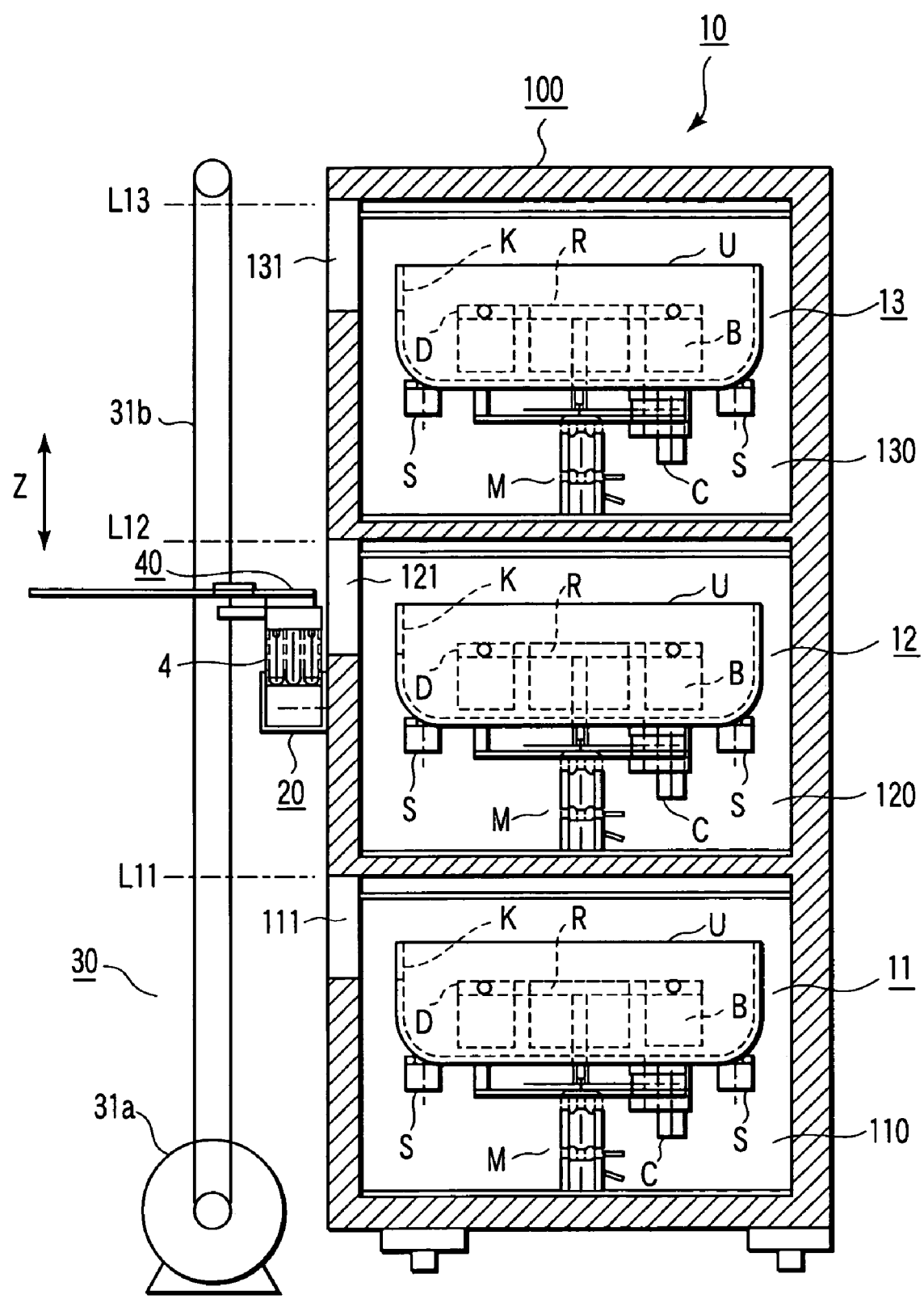
F I G. 3

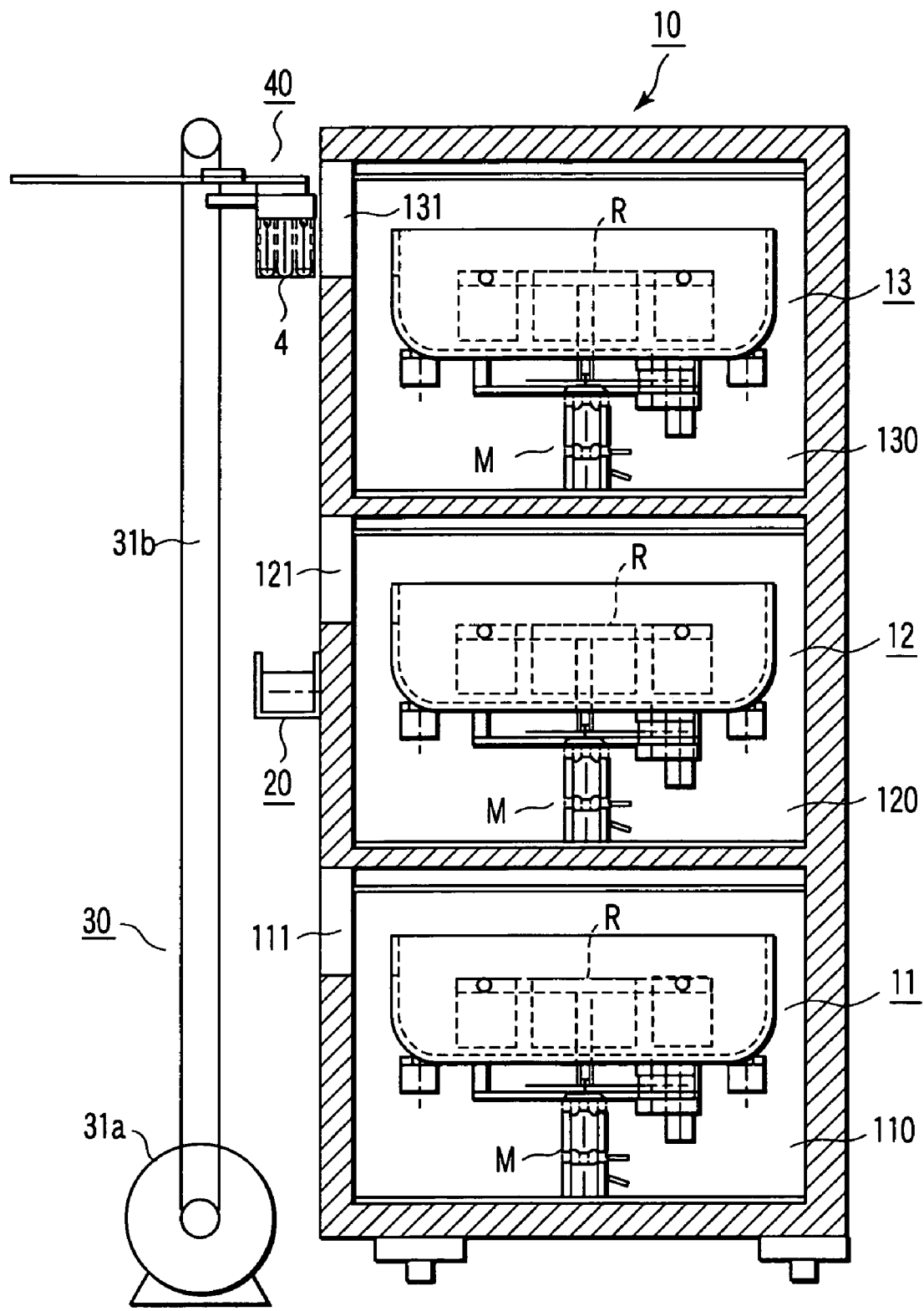
F I G. 4

SPECIMEN CENTRIFUGE SYSTEM

CROSS-REFERENCE TO RELATED APPLICATIONS

This application is based upon and claims the benefit of priority from the prior Japanese Patent Application No. 2002-318702, filed Oct. 31, 2002, the entire contents of which are incorporated herein by reference.

BACKGROUND OF THE INVENTION

1. Field of the Invention

The present invention relates to a specimen centrifuge system for use in a specimen testing center and the like.

2. Description of the Related Art

A specimen centrifuge apparatus configured as follows is proposed as one for use in a specimen testing center and the like (see Jpn. Pat. Appln. KOKAI Publication No. 2000-84436). This apparatus includes first and second rotors. While one of the rotors is centrifuging a specimen, the other rotor replaces a specimen-contained tube with another one.

The above specimen centrifuge apparatus is capable of centrifuging a specimen with efficiency. However, the apparatus requires a relatively large space because the first and second rotors need to be arranged together on the horizontal surface. The apparatus is difficult to centrifuge a number of specimens at once because its centrifuging capacity is restricted. Even when the number of specimens to be centrifuged is very small, the apparatus needs to be operated, and it is therefore likely that energy will be consumed in vain.

BRIEF SUMMARY OF THE INVENTION

An object of the present invention is to provide a specimen centrifuge system having the following advantages.

1) The system has a large centrifuging capacity.

2) The space for the system is small.

3) Even though the number of specimen containers to be centrifuged is small or large, the system can centrifuge them with efficiency.

In order to attain the above object, a specimen centrifuge system according to an aspect of the present invention has the following characteristic configuration. The other characteristic configurations will be clarified in the embodiments later.

A specimen centrifuge system according to an aspect of the present invention, comprises a centrifuge unit including a plurality of specimen centrifuges which are stacked in a plurality of layers in a vertical direction, a rack conveyor which is provided along a horizontal conveyance line that passes by the centrifuge unit convey a specimen-container rack containing a plurality of specimen containers, and a rack elevator which is provided along a vertical conveyance line that passes by the specimen centrifuges in the centrifuge unit to convey the specimen-container rack containing the specimen containers, wherein the rack elevator has a robot arm device which moves the specimen-container rack from the rack conveyor to the rack elevator and from the rack elevator to the rack conveyor and moves the specimen-container rack from the rack elevator to one of the specimen centrifuges and from one of the specimen centrifuges to the rack elevator.

BRIEF DESCRIPTION OF THE SEVERAL VIEWS OF THE DRAWING

FIG. 3 is a longitudinal sectional view taken along double-headed arrow 3—3 shown in FIG. 1.

FIG. 4 is a longitudinal sectional view illustrating an operation of the specimen centrifuge system according to the first embodiment of the present invention, in which a specimen-container rack is conveyed to a designated specimen centrifuge by a rack elevator.

DETAILED DESCRIPTION OF THE INVENTION

First Embodiment

Figure 1:
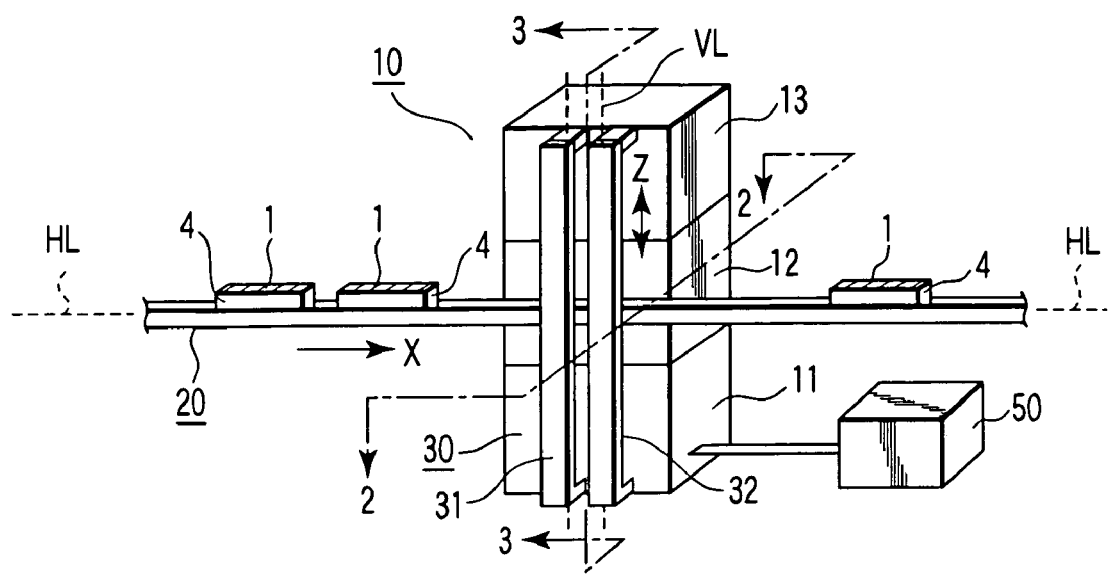
FIG. 1 is a schematic perspective view of a specimen centrifuge system according to a first embodiment of the present invention.
Figure 2:
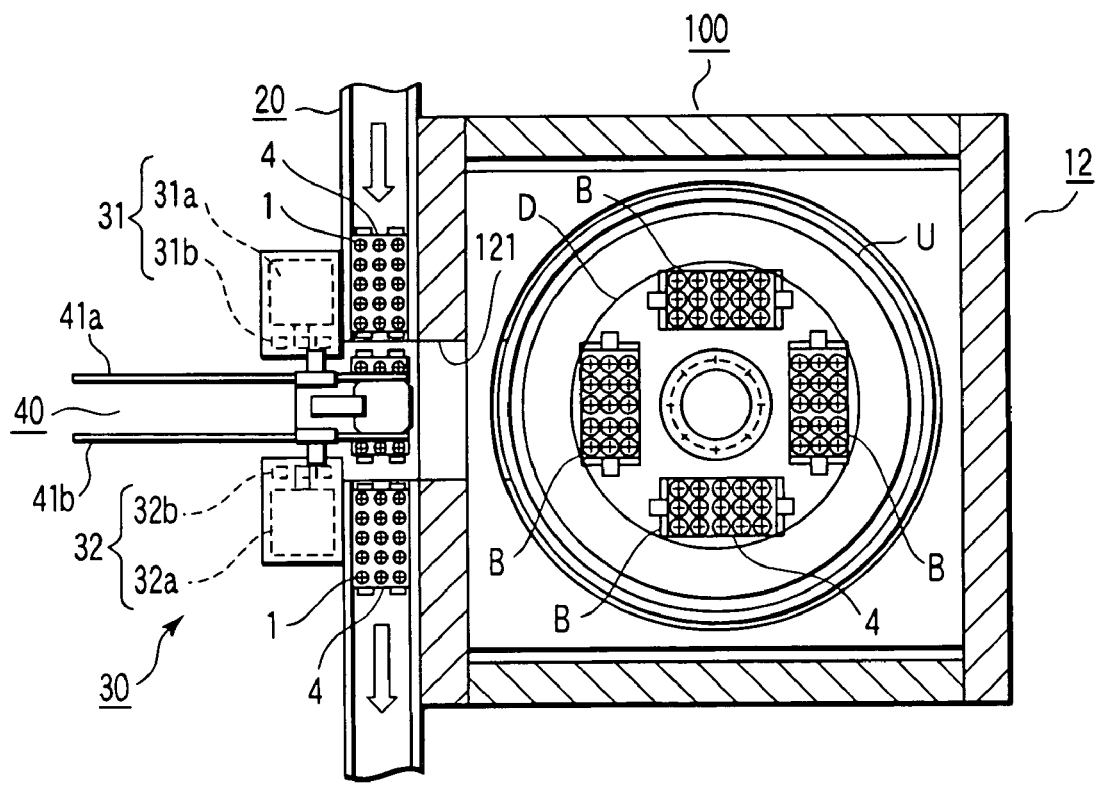
FIG. 2 is a cross-sectional view taken along double-headed arrow 2—2 shown in FIG. 1.

Referring to FIGS. 1 to 3, a specimen centrifuge system according to a first embodiment comprises a centrifuge unit 10. The centrifuge unit 10 includes a plurality of specimen centrifuges 11, 12 and 13 (three in the first embodiment). The specimen centrifuges are vertically stacked in a plurality of layers (three in the first embodiment).

The specimen centrifuges 11, 12 and 13 are stored in first to third cabinets 110, 120 and 130, respectively. These cabinets are formed by partitioning a rectangular parallelepiped housing 100 into three as shown in FIG. 3. The specimen centrifuges 11, 12 and 13 have the same configuration and each have an autobalance function.

Each of the specimen centrifuges 11, 12 and 13 has a motor M that is set up on the floor of the corresponding cabinet. Each of the centrifuges 11, 12 and 13 also has a rotor R that is rotated by the motor M, a protection frame U that surrounds the rotor R, a support member S that supports the protection frame U from below, and a position sensor C that senses a position of the rotation of the rotor R and positions the rotor R to easily load and unload specimen-container racks 2 (described later).

The rotor R has a plurality of buckets B (four in the first embodiment) near the circumference of a rotating disc D. The buckets B can store the specimen-container racks 2. The top ends of the buckets B are supported against the circumference of the disc D with shafts such that the buckets B can swing freely in their entirety. If the rotating disc D rotates at high speed, the bottoms of the buckets B are swung up in the radial direction of the disc D by centrifugal force.

The specimen centrifuges 11, 12 and 13 can be operated independently. A controller 50 controls a simultaneous operation and selective operation of the specimen centrifuges 11, 12 and 13. The controller 50 also controls the centrifuges 11, 12 and 13 that the rotation direction of the rotor R in each layer can be set in a given direction.

The cabinets 110, 120 and 130 have windows 111, 121 and 131 on their front walls. The specimen-container racks 4 can be inserted and removed through the windows 111, 121 and 131. Similarly, the protection frames U have notches K in positions corresponding to the windows 111, 121 and 131. The specimen-container racks 4 can also be inserted and removed through the notches K.

A rack conveyor 20 is provided along a horizontal conveyance line HL that passes by the centrifuge unit 10. The rack conveyor 20 is, for example, a belt conveyor that is capable of conveying the specimen-container racks 4 in the horizontal direction as indicated by arrow X in FIG. 1. Each of the racks 4 is so configured that it can hold and store a plurality of (fifteen in the first embodiment) specimen containers 1 such as test tubes.

A rack elevator 30 is provided in front of the centrifuge unit 10 along a vertical conveyance line VL that passes by the specimen centrifuges 11, 12 and 13. The rack elevator 30 can convey the specimen-container racks 4, which store the specimen containers 1, in the vertical direction as indicated by double-headed arrow Z in FIG. 3. The rack elevator 30 includes a pair of hoisting and lowering mechanisms 31 and 32 that are arranged at regular intervals. The mechanism 31 has a drive motor 31a and an endless belt 31b, and the mechanism 32 has a drive motor 32a and an endless belt 32b. The endless belts 31b and 32b are opposed in parallel to each other. A robot arm device 40 is located between the hoisting and lowering mechanisms 31 and 32 and its both sides are coupled to their corresponding portions of the mechanisms 31 and 32 on the same level. When the mechanisms 31 and 32 are driven at the same time, the robot arm device 40 is hoisted and lowered by the endless belts 31b and 32b with its both sides supported by the mechanisms. The controller 50 controls the robot arm device 40 such that the robot arm device can stop exactly in positions corresponding to levels L11, L12 and L13. Consequently, the specimen-container racks 2 to be conveyed are operated to move in positions opposite to the windows 111, 121 and 131 of the specimen centrifuges 11, 12 and 13.

The robot arm device 40 has a pair of arms 41a and 41b. These arms 41a and 41b can move in a three-dimensional direction and hold and raise the specimen-container racks 4 at their ends. Therefore, the arms 41a and 41b can move the specimen-container racks 4 from the rack conveyor 20 to the rack elevator 30 and vice versa. The arms 41a and 41b can also move the specimen-container racks 2 from the rack elevator 30 to a designated one of the specimen centrifuges 11, 12 and 13 and vice versa.

An operation of the above specimen centrifuge system according to the first embodiment will now be described.

A specimen-container rack 4 that stores fifteen specimen containers 1 each containing a specimen to be centrifuged is conveyed by the rack conveyor 20 along the horizontal conveyance line HL as indicated by arrow X. When the specimen-container rack 4 is conveyed to the location of the centrifuge unit 10, it stops temporarily. Then, the rack 4 is caught by the arms 41a and 41b of the robot arm device 40 attached to the rack elevator 30 and moved from the rack conveyor 20 to the rack elevator 30. The rack elevator 30 operates to move the rack 4 to the front of one (e.g., the centrifuge 13) of the centrifuges 11, 12 and 13, which is designated by a host computer (not shown), as illustrated in FIG. 4.

Figure 5:
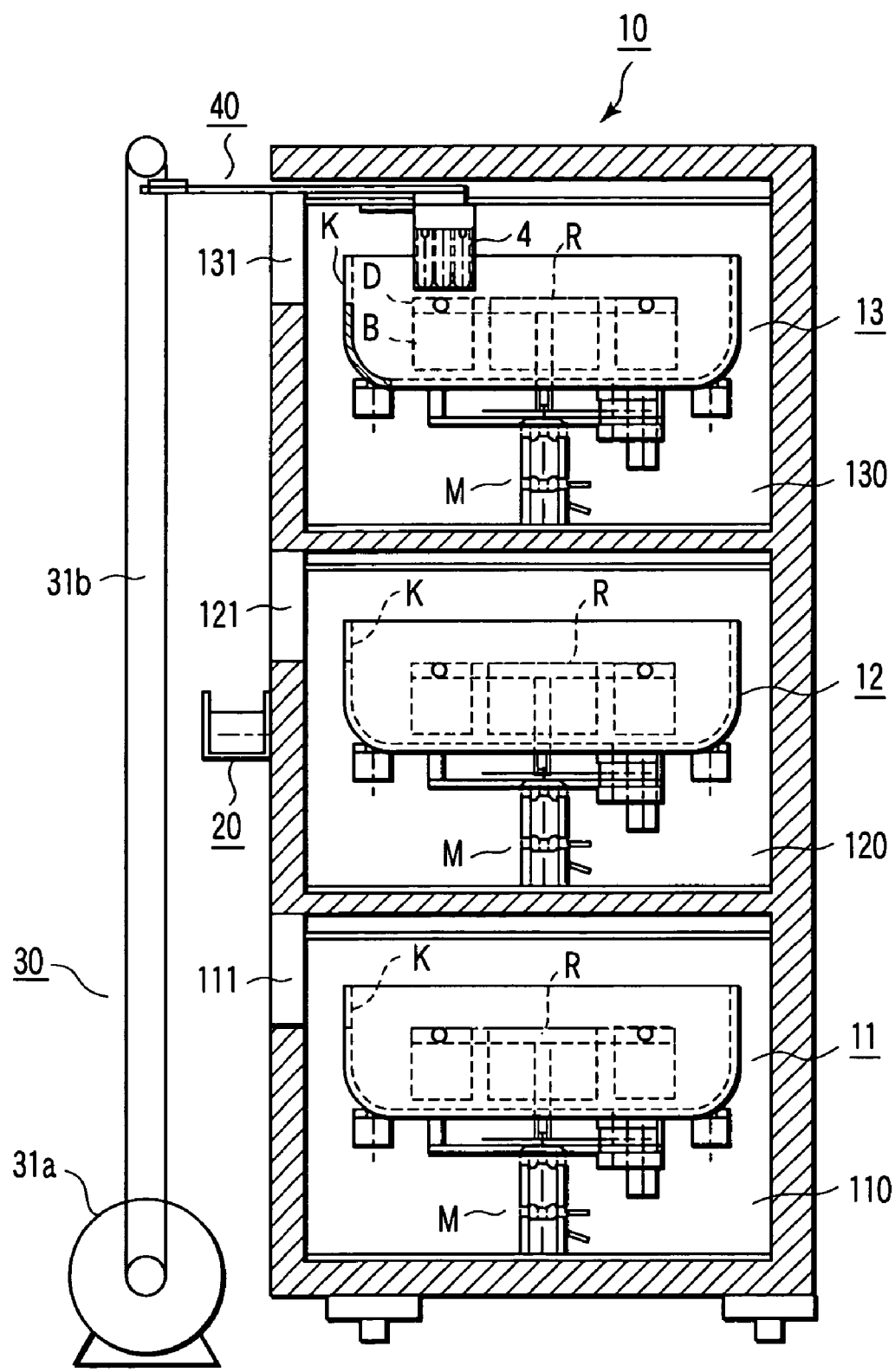
FIG. 5 is a longitudinal sectional view illustrating an operation of the specimen centrifuge system according to the first embodiment of the present invention, in which a specimen-container rack is loaded into a bucket of the designated specimen centrifuge by a robot arm device.

Referring to FIG. 5, the specimen-container rack 4 moved to the centrifuge 13 is transferred to a position above the rotor R of the specimen centrifuge 13 in the cabinet 130 by the protrusion of the arms 41a and 41b. Then, the rack 4 is loaded into one of the buckets B by the catch-release operation of the arms 41a and 41b.

By repeating the above operation, the loading of the specimen-container racks 4 into the buckets B of the rotor R of the specimen centrifuge 13 is completed.

Figure 6:
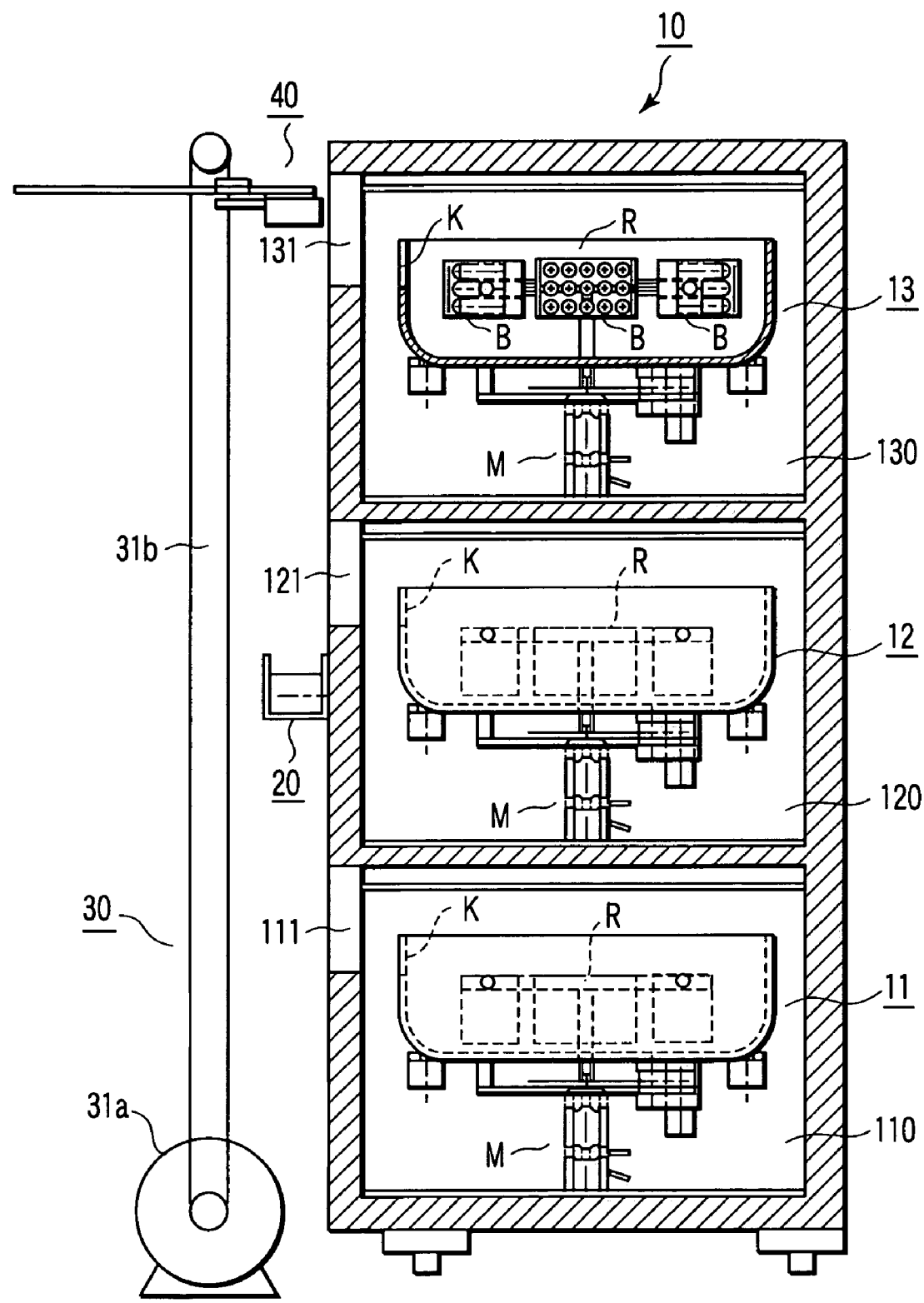
FIG. 6 is a longitudinal sectional view illustrating an operation of the specimen centrifuge system according to the first embodiment of the present invention, in which a specimen-container rack is centrifuged by the designated specimen centrifuge.

After that, other specimen-container racks 4 are loaded into the centrifuges 12 and 11. If the loading of specimen-container racks 4 into all the centrifuges 11, 12 and 13 is completed or the specimen-container racks 4 to be loaded run out, the loading operation is completed. The arms 41a and 41b of the robot arm device 40 are pulled out of the cabinet as shown in FIG. 6.

In the above state, all the specimen centrifuges 11, 12 and 13 start to operate at the same time or only a designated one of the centrifuges start to operate. Consequently, the specimens in the specimen containers 1 stored in the specimen-container racks 4 are centrifuged. This centrifuge operation is performed for about five minutes at a preset rotation speed (which is achieved when the acceleration of gravity applied to the specimen container 1 mounted on the circumference of the rotating disc D having a given diameter becomes 2000 G).

The specimen-container racks 4 whose specimens have been centrifuged in the specimen centrifuges 11, 12 and 13 in the centrifuge unit 10 are moved to the rack elevator 30 and then to the rack conveyor 20 by the procedure reverse to that described above. The centrifuging operation is thus completed.

It takes about two minutes and thirty seconds to perform an operation of loading the specimen-container racks 4 into one specimen centrifuge and unloading them therefrom in addition to an operation of positioning the rotor of the centrifuge. Further, it takes five minutes to perform a centrifuging operation in the specimen centrifuge. The total time required for performing a centrifuging operation once in one specimen centrifuge is therefore about seven minutes and thirty seconds. The centrifuging operation can be performed eight times per hour. Consequently, the number of specimen containers to be processed per hour by one specimen centrifuge is 480 (=15×4×8). In the first embodiment, the three specimen centrifuges 11, 12 and 13 are stacked in layers; therefore, the total number of specimen containers to be processed per hour is 1440 (=480×3)

Second Embodiment

Figure 7:
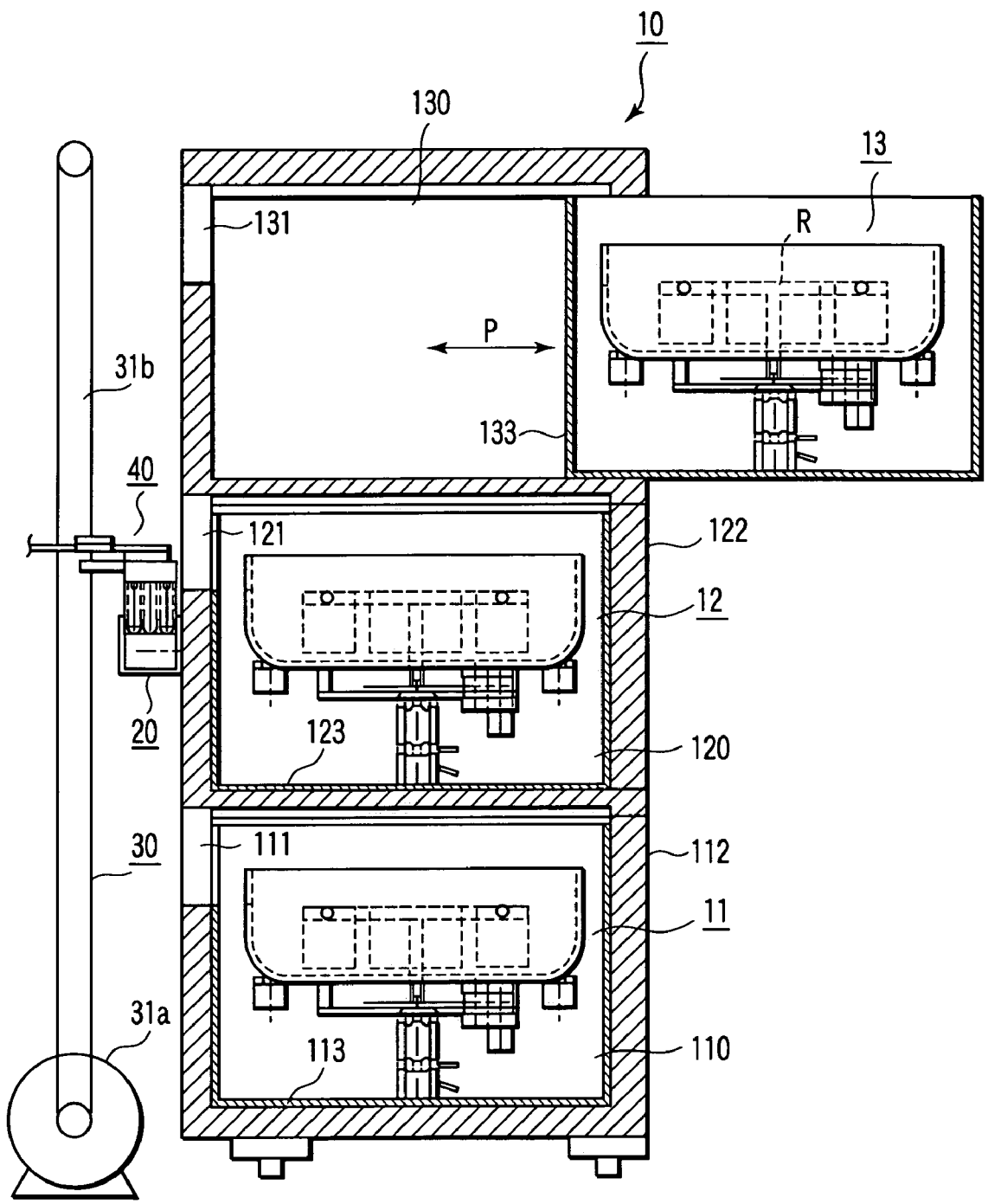
FIG. 7 is a longitudinal sectional view showing a specimen centrifuge system according to a second embodiment of the present invention, which corresponds to FIG. 3.

FIG. 7 is a longitudinal sectional view showing a centrifuge unit 10 according to a second embodiment of the present invention. The second embodiment differs from the first embodiment in which specimen centrifuges 11, 12 and 13 are insertably and removably stored in their respective cabinets 110, 120 and 130 stacked in layers. More specifically, the rear walls of the cabinets 110, 120 and 130 are formed of lids 112, 122 and 132 (not shown) that can freely be opened and closed. Inner boxes 113, 123 and 133 containing the specimen centrifuges 11, 12 and 13 can be slid into and out of the cabinets 110, 120 and 130 in the directions of double-headed arrow P. Thus, for example, the specimen centrifuge 13 can be drawn out, as shown in FIG. 7, to perform predetermined maintenance.

Features of the Embodiments

[1] A specimen centrifuge system according to an embodiment of the present invention, comprises:

a centrifuge unit 10 including a plurality of (three in the embodiment) specimen centrifuges 11, 12 and 13 which are stacked in a plurality of layers in a vertical direction;

a rack conveyor 20 which is provided along a horizontal conveyance line HL that passes by the centrifuge unit 10 to convey a specimen-container rack 4 containing a plurality of (fifteen in the embodiment) specimen containers 1; and a rack elevator 30 which is provided along a vertical conveyance line VL that passes by the specimen centrifuges 11, 12 and 13 in the centrifuge unit 10 to convey the specimen-container rack 4 containing the specimen containers 1, wherein the rack elevator 30 has a robot arm device 40 which moves the specimen-container rack 4 from the rack conveyor 20 to the rack elevator 30 and from the rack elevator 30 to the rack conveyor 20 and moves the specimen-container rack 4 from the rack elevator 30 to one of the specimen centrifuges 11, 12 and 13 and from one of the specimen centrifuges 11, 12 and 13 to the rack elevator 30.

The specimen centrifuge system described above comprises a centrifuge unit 10 including a plurality of (three in the embodiment) specimen centrifuges 11, 12 and 13 which are stacked in a plurality of layers in the vertical direction. It is thus possible to achieve a large centrifuging capacity corresponding to the total number of specimen centrifuges 11, 12 and 13. A space for only one specimen centrifuge is large enough to set up the three specimen centrifuges. The minimum space has only to be secured to set up the specimen centrifuges.

[2] In the specimen centrifuge system described in above item [1], the specimen centrifuges 11, 12 and 13 are operated independently and operated simultaneously or selectively by a controller 50.

In the specimen centrifuge system described above, since an arbitrary one of the specimen centrifuges 11, 12 and 13 can selectively be operated, a minimum specimen centrifuge has only to be operated in accordance with the number of specimen-container racks 4 conveyed by the conveyor 20. Consequently, the centrifuging operation can be performed with efficiency.

[3] In the specimen centrifuge system described in above item [1], the specimen centrifuges 11, 12 and 13 each have a rotor R whose rotation direction is set in a given direction by a controller 50.

In the foregoing specimen centrifuge system, the rotation directions of the rotors R in the respective layers can be set opposite alternately. When the rotation direction of rotors R are set opposite alternately, the mechanical vibrations of the specimen centrifuges 11, 12 and 13 interfere with one another. Thus, the specimen centrifuges 11, 12 and 13 can be reduced in noise and increased in lifetime.

[4] In the specimen centrifuge system described in one of above items [1] and [2], the specimen centrifuges 11, 12 and 13 are insertably and removably stored in cabinets 110, 120 and 130 that are provided in respective layers.

In the above specimen centrifuge system, a desired one of the specimen centrifuges 11, 12 and 13 can be drawn out of its corresponding cabinet. It is thus easy to perform maintenance of the specimen centrifuges 11, 12 and 13.

Modifications

The specimen centrifuge system according to an embodiment of the present invention includes the following modifications.

1) Four or more specimen centrifuges are stacked in layers.

2) A plurality of rack elevators are provided.

What is claimed is:

1. A specimen centrifuge system comprising:
a centrifuge unit including a plurality of cabinets which are stacked in a plurality of layers in a vertical direction, the cabinets storing specimen centrifuges, a wall of the cabinets being opened and closed through which the specimen centrifuges are insertably and removably stored in the cabinets;
a rack conveyor which conveys a specimen-container rack containing a plurality of specimen containers to the centrifuge unit; and
a rack elevator which conveys the specimen-container rack to one of the specimen centrifuges,
wherein the rack elevator has an elevator provided at a side of the centrifuge unit and a robot arm device which is lifted up and down by the elevator and horizontally conveys the specimen-container rack to one of the specimen centrifuges.

2. The specimen centrifuge system according to claim 1, wherein the specimen centrifuges are operated independently and operated simultaneously or selectively by a controller.

3. The specimen centrifuge system according to claim 1, wherein the specimen centrifuges each have a rotor whose rotation direction is set in a given direction by a controller.

4. The specimen centrifuge system according to claim 1, wherein the cabinet comprises a window for each of the specimen centrifuges, and the robot arm device is positionable by the rack elevator to load the specimen containers in the specimen centrifuges via the windows, respectively.

* * * * *